(12) United States Patent
Greuet et al.

(10) Patent No.: US 10,191,177 B2
(45) Date of Patent: Jan. 29, 2019

(54) APPARATUS AND A METHOD FOR METAL DETECTION INVOLVING A MOBILE TERMINAL WITH A DISPLAY

(75) Inventors: Jean-Baptiste Greuet, Ulm (DE); Cieslak Lars, Ulm (DE); Koray Ozcan, Farnborough (GB)

(73) Assignee: Nokia Technologies Oy, Espoo (FI)

( * ) Notice: Subject to any disclaimer, the term of this patent is extended or adjusted under 35 U.S.C. 154(b) by 638 days.

(21) Appl. No.: 14/357,567

(22) PCT Filed: Nov. 11, 2011

(86) PCT No.: PCT/IB2011/055050
§ 371 (c)(1),
(2), (4) Date: Aug. 5, 2014

(87) PCT Pub. No.: WO2013/068795
PCT Pub. Date: May 16, 2013

(65) Prior Publication Data
US 2014/0375310 A1 Dec. 25, 2014

(51) Int. Cl.
| | |
|---|---|
| *G01R 33/02* | (2006.01) |
| *G01V 3/10* | (2006.01) |
| *G01R 33/028* | (2006.01) |
| *G06F 3/046* | (2006.01) |
| *G01V 3/15* | (2006.01) |
| *G01N 27/72* | (2006.01) |
| *H04M 1/21* | (2006.01) |
| *G01R 33/12* | (2006.01) |

(52) U.S. Cl.
CPC ............. *G01V 3/101* (2013.01); *G01N 27/72* (2013.01); *G01R 33/0206* (2013.01); *G01R 33/028* (2013.01); *G01V 3/104* (2013.01); *G01V 3/15* (2013.01); *G06F 3/046* (2013.01); *H04M 1/21* (2013.01); *G01R 33/1215* (2013.01)

(58) Field of Classification Search
CPC .. B64G 1/366; G01R 33/0206; G01R 33/028; G01R 33/038; G01R 33/1215
USPC ..................... 324/51, 55, 200, 227, 228–244
See application file for complete search history.

(56) References Cited

U.S. PATENT DOCUMENTS

| | | | |
|---|---|---|---|
| 4,390,836 A | 6/1983 | Bruce et al. | |
| 2002/0163346 A1* | 11/2002 | Arndt | G01V 3/104 324/639 |
| 2004/0155651 A1* | 8/2004 | Britton | G01V 3/107 324/243 |
| 2004/0214598 A1 | 10/2004 | Parameswaran Rajamma | |

(Continued)

FOREIGN PATENT DOCUMENTS

WO   0065379 A1   11/2000

OTHER PUBLICATIONS

International Search Report received for corresponding Patent Cooperation Treaty Application No. PCT/IB2011/055050, dated Aug. 24, 2012, 5 pages.

*Primary Examiner* — Jermele M Hollington
*Assistant Examiner* — Raul Rios Russo
(74) *Attorney, Agent, or Firm* — Harrington & Smith

(57) ABSTRACT

An apparatus comprising at least one first signal loop configured to receive a first signal; at least one second signal loop magnetically coupled with the first signal loop configured to generate a second signal; a signal processor configured to monitor the second signal and determine the presence of at least one metal object dependent on the second signal.

29 Claims, 13 Drawing Sheets

(56) References Cited

U.S. PATENT DOCUMENTS

| | | | |
|---|---|---|---|
| 2004/0254453 A1* | 12/2004 | Govari | A61B 5/062 |
| | | | 600/424 |
| 2005/0179543 A1* | 8/2005 | Lian | G08B 29/046 |
| | | | 340/540 |
| 2006/0148519 A1 | 7/2006 | Simpson et al. | |
| 2007/0188158 A1 | 8/2007 | Skultety-Betz | |
| 2008/0055080 A1* | 3/2008 | Britton | G01V 3/107 |
| | | | 340/551 |
| 2008/0109189 A1* | 5/2008 | Bauer | G01D 5/202 |
| | | | 702/189 |
| 2008/0117044 A1* | 5/2008 | Hibbs | G01V 3/105 |
| | | | 340/568.1 |
| 2008/0278154 A1 | 11/2008 | Krapf et al. | |
| 2009/0160790 A1 | 6/2009 | Fukushima et al. | |
| 2009/0167300 A1* | 7/2009 | Cech | B60R 21/0134 |
| | | | 324/239 |
| 2009/0319212 A1* | 12/2009 | Cech | B60R 21/0136 |
| | | | 702/65 |
| 2009/0322321 A1* | 12/2009 | Schiefele | G01R 33/18 |
| | | | 324/228 |
| 2011/0171910 A1* | 7/2011 | Dinh | G08B 13/2402 |
| | | | 455/63.1 |
| 2011/0273301 A1* | 11/2011 | Dinh | G01V 3/10 |
| | | | 340/600 |
| 2012/0077537 A1* | 3/2012 | Muratov | H04B 5/0037 |
| | | | 455/522 |
| 2012/0321115 A1* | 12/2012 | Jylanki | H04B 5/0087 |
| | | | 381/331 |

* cited by examiner

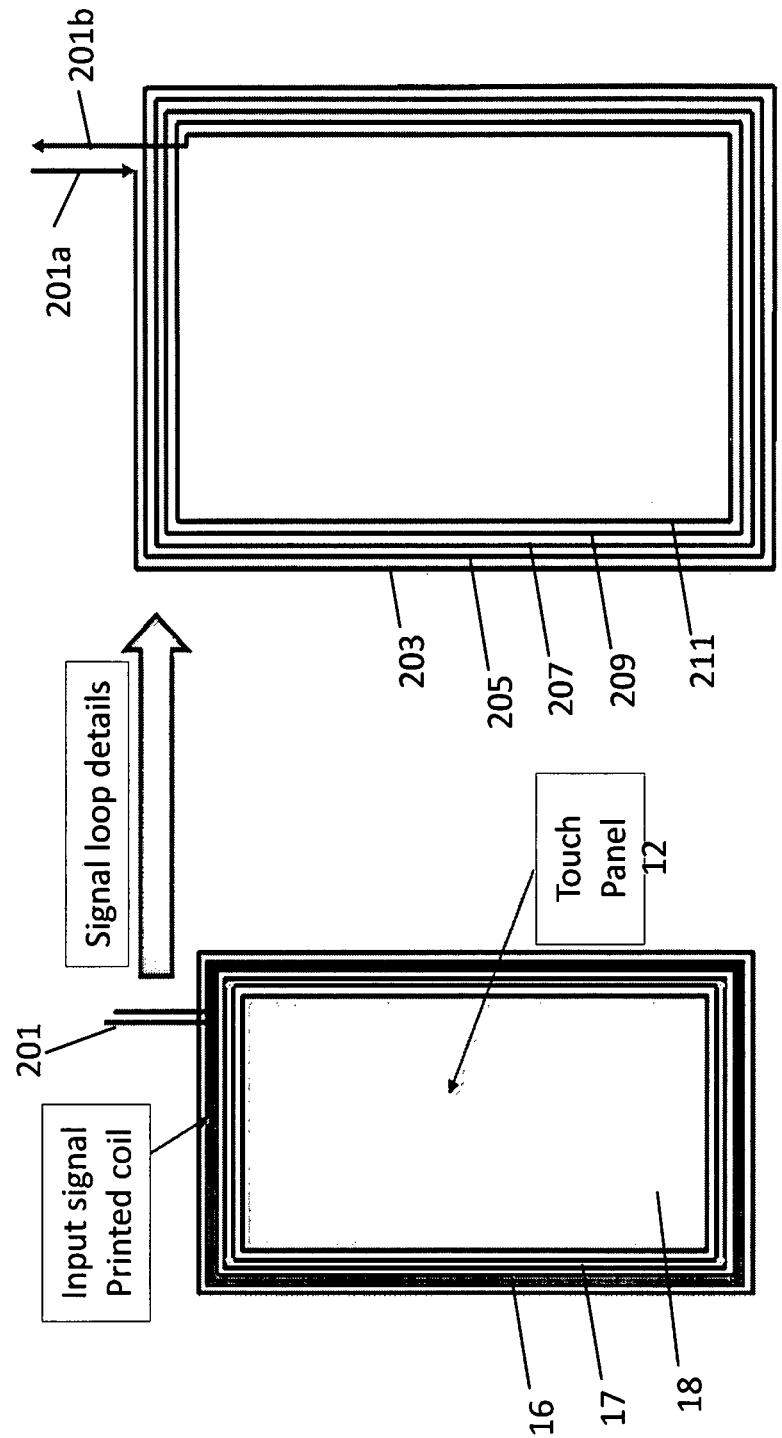

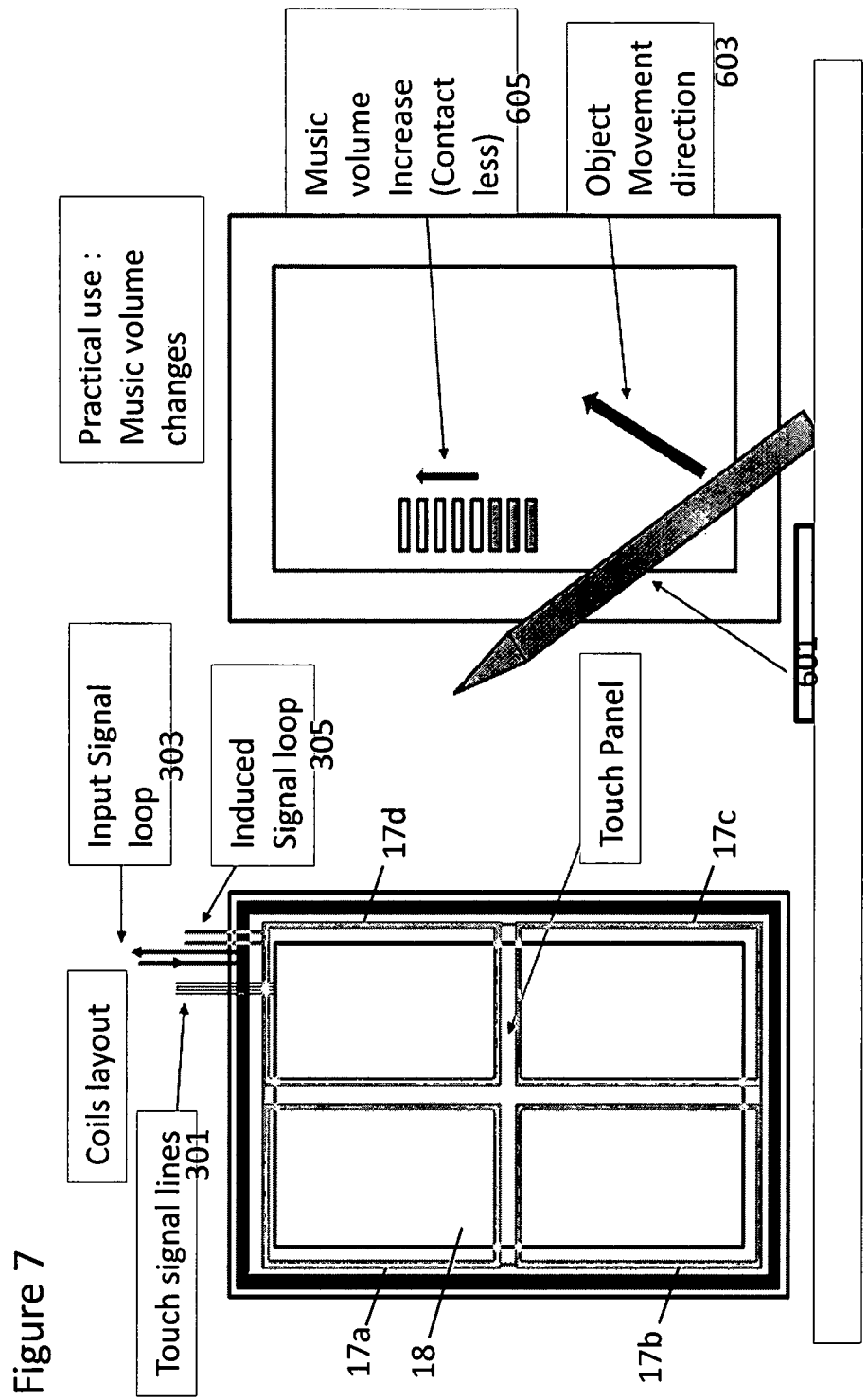

Steel

Reference (no metal)

Magnesium

Brass

APPARATUS AND A METHOD FOR METAL DETECTION INVOLVING A MOBILE TERMINAL WITH A DISPLAY

RELATED APPLICATION

This application was originally filed as PCT Application No. PCT/IB2011/055050 filed Nov. 11, 2011.

FIELD OF THE APPLICATION

The present invention relates to apparatus for metal detection. The invention further relates to, but is not limited to, apparatus for metal detection in user equipment.

BACKGROUND OF THE APPLICATION

Electronic devices such as user equipment and mobile phones are well known. The user experience of an electronic device is largely related to the look and feel of the operation of the device. This look and feel of the operation of the device is often reflected by the user interface. User interfaces come in many different forms and functions, and can include inputs such as keys, buttons, touchscreen, audio and visual and outputs such as auditory, visual and tactile and other interfaces.

User interfaces for example can be used to trigger functionality within the device or apparatus. For example a key press or touchscreen 'virtual key' press can trigger an application such as opening an email client, or enable or activate a component of the device such as a Bluetooth transceiver to open a connection to be made with a separate device or apparatus.

Metal detection by magnetic field induction interference is also known and has been incorporated into apparatus which is typically bulky.

Similarly a user can by operating the user interface enable an application or program within the device to operate.

SUMMARY OF SOME EMBODIMENTS

There is provided according to a first aspect an apparatus comprising: at least one first signal loop configured to receive a first signal; at least one second signal loop magnetically coupled with the first signal loop configured to generate a second signal; a signal processor configured to monitor the second signal and determine the presence of at least one metal object dependent on the second signal.

The first signal loop may comprise a conductive material adjacent to and at least partially surrounding an apparatus display.

The second signal loop may comprise a conductive material adjacent to and at least partially surrounding an apparatus display.

At least one of the first signal loop and the second signal loop may be formed from a part of the other of the second signal loop and the first signal loop respectively.

The first signal may comprise at least one of: an amplitude modulated signal; a frequency modulated signal; and an interrupted wave modulated signal.

The first signal may comprise a swept signal having a first frequency range.

The second signal may comprise a resonance profile signal.

The resonance profile signal may comprise at least one of: at least one resonance frequency; at least one associated resonance frequency amplitude; and at least one associated resonance frequency quality factor.

The signal processor may be configured to determine a difference between a reference resonance profile signal and the resonance profile signal to determine the presence of at least one metallic object.

The apparatus may further comprise a memory configured to store the reference resonance profile signal.

The apparatus may further comprise a memory configured to include at least one memorized resonance profile signal associated with an identified metal; wherein the signal processor is configured to determine the at least one metallic object is the identified metal when the resonance profile signal at least partially matches the at least one memorized resonance profile signal.

The signal processor may be further configured to determine dependent on the second signal at least one of: a composition of metals in the object; a location of the metal object; and an orientation of the metal object.

The at least one second signal loop may comprise at least two second signal loops, each of the second signal loops located or orientated differently to each other, such that the a signal processor is configured to determine the motion of the at least one metal object dependent on the second signal from each of the second signal loops.

The apparatus may further comprise a controller configured to control the apparatus dependent on determining the presence of at least one metal object.

The apparatus may further comprise a user interface output wherein the controller is configured to control the user interface output dependent on the determining the presence of at least one metal object.

The user interface output may comprise at least one of: a display configured to change dependent on the determining the presence of at least one metal object; a speaker configured to output a tone dependent on the determining the presence of at least one metal object; a light configured to output a light dependent on the determining the presence of at least one metal object; and a vibra configured to vibrate dependent on the determining the presence of at least one metal object.

The apparatus may further comprise a transceiver wherein the controller is configured to control the transceiver dependent determining the presence of at least one metal object.

The transceiver may be a Bluetooth transceiver, wherein the controller may be configured to initiate a communications coupling with a carkit transceiver dependent on the signal processor determining the presence of at least one metal object within a carkit apparatus holder configured to hold the apparatus.

A car may comprise the apparatus as discussed herein.

A tractor may comprise the apparatus as discussed herein, wherein the tractor is configured to detect the presence of at least one metallic object in the soil over which the tractor is located.

According to a second aspect there is provided a method comprising: receiving a first signal in at least one first signal loop; generating a second signal in at least one second signal loop magnetically coupled with the first signal loop; and determining the presence of at least one metal object dependent on the second signal.

The method may further comprise providing the first signal loop as a conductive material adjacent to and at least partially surrounding an apparatus display.

The method may further comprise providing the second signal loop as a conductive material adjacent to and at least partially surrounding an apparatus display.

The method may further comprise providing a signal loop as a conductive material wherein the first signal loop and the second signal loop are formed from the signal loop.

The first signal may comprise at least one of: an amplitude modulated signal; a frequency modulated signal; and an interrupted wave modulated signal.

The first signal may comprise a swept signal having a first frequency range.

The second signal may comprise a resonance profile signal.

The resonance profile signal may comprise at least one of: at least one resonance frequency; at least one associated resonance frequency amplitude; and at least one associated resonance frequency quality factor.

Determining the presence of at least one metal object dependent on the second signal may comprise determining a difference between a reference resonance profile signal and the resonance profile signal to determine the presence of at least one metallic object.

The method may comprise storing the reference resonance profile signal.

The method may further comprise associating at least one memorized resonance profile signal with an identified metal; wherein determining the presence of at least one metal object dependent on the second signal may comprise determining the metal object is the identified metal when the resonance profile signal at least partially matches the at least one memorized resonance profile signal.

Determining the presence of at least one metal object dependent on the second signal may comprise at least one of: determining a composition of metals in the object; determining a location of the metal object; and determining an orientation of the metal object.

The method may further comprise providing at least two second signal loops, wherein each of the second signal loops are located or orientated differently to each other; wherein determining the presence of at least one metal object dependent on the second signal may comprise determining a motion of the at least one metal object dependent on the second signal from each of the second signal loops.

The method may comprise controlling an apparatus dependent on determining the presence of at least one metal object.

Controlling an apparatus dependent on determining the presence of at least one metal object may comprise controlling an user interface output dependent on the determining the presence of at least one metal object.

Controlling an user interface output dependent on the determining the presence of at least one metal object may comprise at least one of: changing a display dependent on the determining the presence of at least one metal object; outputting a tone from a speaker dependent on the determining the presence of at least one metal object; outputting a light dependent on the determining the presence of at least one metal object; and vibrating a vibra dependent on the determining the presence of at least one metal object.

Controlling a user interface output dependent on the determining the presence of at least one metal object may comprise controlling a transceiver dependent determining the presence of at least one metal object.

Controlling a transceiver dependent determining the presence of at least one metal object may comprise initiating at a Bluetooth transceiver a communications coupling with a carkit transceiver dependent on the signal processor determining the presence of at least one metal object within a carkit apparatus holder.

A car may be configured to perform the method as discussed herein.

A tractor may be configured to detect the presence of at least one metallic object in the soil over which the tractor is located according to a method as discussed herein.

According to a third aspect there is provided an apparatus comprising: means for receiving a first signal in at least one first signal loop; means for generating a second signal in at least one second signal loop magnetically coupled with the first signal loop; and means for determining the presence of at least one metal object dependent on the second signal.

The apparatus may further comprise means for providing the first signal loop as a conductive material adjacent to and at least partially surrounding an apparatus display.

The apparatus may further comprise means for providing the second signal loop as a conductive material adjacent to and at least partially surrounding an apparatus display.

The apparatus may further comprise means for providing a signal loop as a conductive material wherein the first signal loop and the second signal loop are formed from the signal loop.

The first signal may comprise at least one of: an amplitude modulated signal; a frequency modulated signal; and an interrupted wave modulated signal.

The first signal may comprise a swept signal having a first frequency range.

The second signal may comprise a resonance profile signal.

The resonance profile signal may comprise at least one of: at least one resonance frequency; at least one associated resonance frequency amplitude; and at least one associated resonance frequency quality factor.

The means for determining the presence of at least one metal object dependent on the second signal may comprise means for determining a difference between a reference resonance profile signal and the resonance profile signal to determine the presence of at least one metallic object.

The apparatus may further comprise means for storing the reference resonance profile signal.

The apparatus may further comprise means for associating at least one memorized resonance profile signal with an identified metal; wherein the means for determining the presence of at least one metal object dependent on the second signal may comprise means for determining the metal object is the identified metal when the resonance profile signal at least partially matches the at least one memorized resonance profile signal.

The means for determining the presence of at least one metal object dependent on the second signal may comprise at least one of: means for determining a composition of metals in the object; means for determining a location of the metal object; and means for determining an orientation of the metal object.

The apparatus may further comprise means for providing at least two second signal loops, wherein each of the second signal loops are located or orientated differently to each other; wherein the means for determining the presence of at least one metal object dependent on the second signal may comprise means for determining a motion of the at least one metal object dependent on the second signal from each of the second signal loops.

The apparatus may further comprise means for controlling an apparatus dependent on determining the presence of at least one metal object.

The means for controlling an apparatus dependent on determining the presence of at least one metal object may comprise means for controlling a user interface output dependent on the determining the presence of at least one metal object.

The means for controlling a user interface output dependent on the determining the presence of at least one metal object may comprise at least one of: means for changing a display dependent on the determining the presence of at least one metal object; means for outputting a tone from a speaker dependent on the determining the presence of at least one metal object; means for outputting a light dependent on the determining the presence of at least one metal object; and means for vibrating a vibra dependent on the determining the presence of at least one metal object.

The means for controlling a user interface output dependent on the determining the presence of at least one metal object may comprise means for controlling a transceiver dependent determining the presence of at least one metal object.

The means for controlling a transceiver dependent determining the presence of at least one metal object may comprise means for initiating at a Bluetooth transceiver a communications coupling with a carkit transceiver dependent on the signal processor determining the presence of at least one metal object within a carkit apparatus holder.

A car may comprise the apparatus as discussed herein.

A tractor may comprise the apparatus as discussed herein configured to detect the presence of at least one metallic object in the soil over which the tractor is located.

BRIEF DESCRIPTION OF DRAWINGS

For better understanding of the present invention, reference will now be made by way of example to the accompanying drawings in which:

FIGS. 3a to 3d show schematically the printed loop sensor component shown in FIGS. 1 and 2 in further detail according to some embodiments;

FIG. 7 shows schematically an example user interface input use for embodiments of the application;

SOME EMBODIMENTS OF THE APPLICATION

Figure 1:
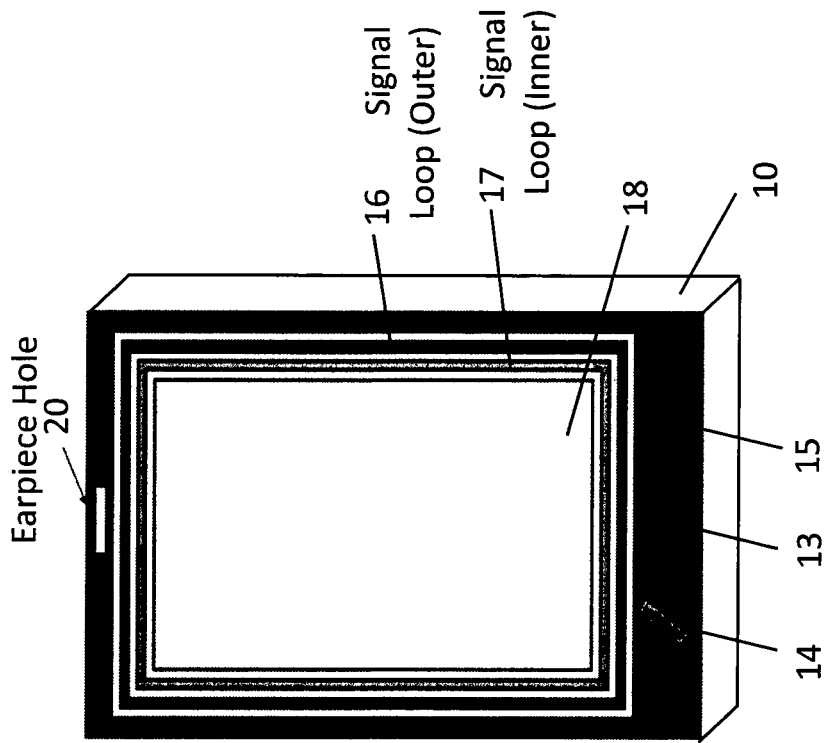
FIG. 1 shows schematically an electronic device employing embodiments of the application.

The following describes apparatus and methods for generating magnetic fields for detecting metal by electronic devices or apparatus. In this regard reference is made to FIG. 1 which shows a schematic diagram of an exemplary electronic device or apparatus 10 which may incorporate metal detection magnetic field generating and sensing components according to some embodiments of the application.

The apparatus can in some embodiments be a mobile terminal or user equipment for a wireless communications system. In some other embodiments the electronic device or apparatus can be an audio player (also known as MP3 players) a media player (also known as MP4 players), or an electronic book reader.

In some other embodiments the apparatus can be any suitable electronic apparatus such as a personal data assistant (PDA), personal computer (such as a netbook, tablet, or other mobile personal computer), or an electronic wallet. The apparatus in some embodiments can be fixed in position or be mobile. Although the following examples typically describe a mobile or portable apparatus, it would be appreciated that some embodiments may be fixed in position, for example an automatic assay machine or automatic teller machine (ATM) apparatus comprising a component similar to those described hereafter would have advantages similar to those described below with respect to mobile apparatus.

It would be further understood that in some embodiments the apparatus can be implemented as electronic components of vehicles. For example the following apparatus can be implemented in cars and other automotive machines. For example the apparatus can be implemented within a tractor so to prevent the tractor from damaging any towed implements from contacting metal under the surface of the soil being worked on. Furthermore some embodiments of the apparatus can be implemented to detect on mobile apparatus such as mine clearing machines to detect buried metallic mines, shells or other ordinance or improvised explosive devices containing metal or close to the surface.

The apparatus 10 comprises in some embodiments an object sensor component 12 mounted on the frame of the apparatus. The object sensor component 12 can be configured to generate and sense a magnetic field suitable for detecting metallic objects.

In the following example the object sensor component is integrated within a touch screen panel and suitable for providing the user with a user interface for inputting touch related data and generating. The touch screen panel implementation of the object sensor component 12 therefore comprises a touch sensitive area 18 configured to detect and relay touch data.

Furthermore the object sensor component 12 in some embodiments comprises a first signal loop, conductive path, or coil 16 and a second signal loop, conductive path or coil 17. In some embodiments, as discussed herein, the first signal loop and the second signal loop can be implemented as a 'single' loop apparatus, in other words a signal loop can be used to implement both the first signal loop and the second signal loop. In the example touch screen panel implementation of the object sensor component shown in FIG. 1 the first signal loop 16 at least partially surrounds the touch sensitive area 18, and a second (inner) conductive path or signal loop 17 which at least partially surrounds the touch sensitive area 18 and is in turn partially surrounded by the first (outer) signal loop 16.

It would be understood that in some embodiments of the application the first and second signal loops can be topologically configured in any suitable manner. For example the signal loops can be arranged side-by-side (or offset in at least one of the x or y dimensions where the loops are in the x-y plane), and/or on top of each other (or in other words offset in the z-dimension from each other where the loops are in the x-y plane). In some embodiments there can furthermore be more than two signal loops.

It would be appreciated that in some embodiments the object sensor component 12 can implement the first and second signal loops in any suitable manner. In the examples described herein the first and second signal loops can also be implemented as conductive pathways implemented onto or in a panel. However it would be understood that the signal loops can be implemented in any suitable manner. For example the signal loops can in some embodiments be separated. In some embodiments the signal loops are loops of conductive material, for example copper wire or suitably drawn conductive material arranged in coil or loop configuration within the apparatus.

The conductive material configured to implement the signal loops can be printed, glued, fixed, embedded, pinned or by any other suitable locating means physically arranged within or on the apparatus. For example the signal loops are implemented as copper coils glued in a separate substrate surrounding parts of the apparatus. For example the loops can be embedded into the casing or cover of the apparatus. The signal loops can further be configured in some embodiments to operate as mutually coupled induction loops for generating and detecting magnetic fields.

In some embodiments loops could be separated and could be copper loops "glued" in a separate substrate that would surround other parts of the phone (for example in a separate cover of the phone). In such embodiments the loops can be multifunctional. For example the copper loop can be used as an antenna (FM radio reception or near field communication NFC), or be used as a communication antenna for example from one loop to another or from the loop to a hearing aid compatible (HAC) device.

In some embodiments where the apparatus display is a liquid crystal display (LCD) technology the conductive material signal loops suitable for providing the generating and sensing induction as described hereafter can be implemented on at least one of the conductive layers used in the liquid crystal display technology. For example the inner and outer signal loops can in some embodiments be implemented on at least the thin film transistor (TFT) layer or the layer used as a contact to provide a potential difference across the LCD cells. It would also be understood that in some embodiments the signal loops can be implemented on any suitable conductive layer used in any suitable display technology, such as contact layers in light emitting diodes, plasma displays and other such layers.

Furthermore although the following examples describe signal loops which partially surround the touch sensitive area it would be appreciated that some other embodiments can feature other configurations. For example in some embodiments the signal loops can also be implemented at least partially within the touch sensitive or display area 18. In such examples the implementation of the touch sensitive or display area is complicated by the implementation of electrical connections or bridges between the touch sensitive areas or islands between the signal loops. It would be understood that in some embodiments the loops can be offset compared to the display area 18. For example in some embodiments the loops may be not axisymmetric as shown in the figures.

In some embodiments the object sensor component 12 signal loops 16, 17 are implemented as perimeter conductive conduits. The perimeter conductive conduits for example where the object sensor component 12 is a part of a display panel or touch screen panel in some embodiments of the application can substantially surround the display and/or touch sensitive area of the touch screen panel. In some embodiments, the signal loops are hidden by the frame of the apparatus casing 10 in such a way that only the apparatus display or touch panel display are visible to the user. In other words in some embodiments the signal loops are hidden or protected against physical damage by the apparatus casing.

The apparatus 10 furthermore in some embodiments comprises input switches or buttons such as input button 1 14, input button 2 13 and input button 3 15 suitable for providing inputs to the apparatus via a user interface other than the touch panel 12.

The apparatus 10 furthermore in some embodiments comprises an earpiece hole 20 enabling the output of acoustic waves generated via an acoustic or audio transducer located within the apparatus 10. In some embodiments the earpiece hole 20 can be part of an integrated hands-free (IHF) audio sub-system configured to produce suitable acoustic waves for hands free operation of the apparatus.

The apparatus can in some embodiments comprise a display component which may be configured to display information. As shown in FIG. 1 the display component is viewable through the object sensing component 12 implemented as a touch screen device either through the touch sensitive area 18 (for example comprising a liquid crystal display unit underneath the touch panel) or in some embodiments the display component can be implemented on the object sensing component 12 for example a screen printed or fixed display used to display characters.

Although the above example features an object sensing component 12 operating as a touch panel component it would be appreciated that the object sensing component can be implemented as a combined touch panel/display component with a capacity for providing display information through or on the touch panels touch sensitive area 18.

Furthermore it would be understood that in some embodiments the signal loops can be implemented as described herein as a signal loop or sensing panel whereby at least one signal loop is implemented on the panel.

The apparatus 10 can in some embodiments comprise a processor which can be coupled or connected via suitable connections to the touch panel component 12.

The apparatus 10 can in some embodiments comprise an audio subsystem configured to output audio signals. The processor can in some embodiments be coupled or connected to the audio subsystem. The audio subsystem in some embodiments can comprise an acoustic or audio transducer, for example as part of a loudspeaker or earpiece, configured to generate acoustic waves dependent on the electronic audio signals passed to the audio subsystem from the processor.

In some embodiments the apparatus comprises a transceiver (TX/RX) which is further coupled or linked to the processor and suitable for transmitting and receiving data with further apparatus via a wireless communication protocol. Any suitable wireless communication protocol can be implemented in embodiments of the application.

The transceiver in some embodiments enables communication with other apparatus, for example, via a cellular or mobile phone gateway service such as a node B or base transceiver station (BTS) and a wireless communications network, or short range wireless communications to other apparatus located remotely from the apparatus.

The apparatus in some embodiments can further comprise a memory to which the processor is coupled. The processor may be configured to execute various program codes. The implemented program codes may in some embodiments control the operation of the signal loops 16 and 17. The implemented program codes can in some embodiments be stored for example in the memory for retrieval by the processor whenever needed. The memory in some embodiments can further provide a section for storing data.

Figure 2:
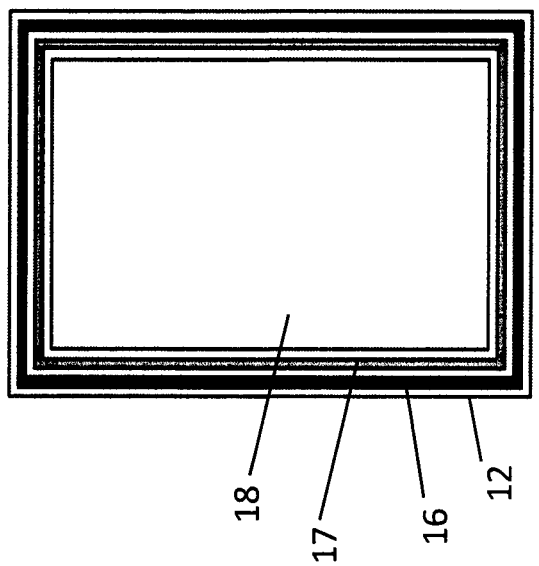
FIG. 2 shows schematically an object sensor component suitable for implementing within FIG. 1 according to some embodiments.

It is understood that the structure of the apparatus 10 can be supplemented and varied in many ways and that the examples shown in FIG. 2 onwards represent only part of the operation of an apparatus comprising exemplary embodiments of the application.

With respect to FIG. 2, a plan view of an object sensing component 12 implemented in some embodiments on a single touch panel component 12 is shown separate from the apparatus shown in FIG. 1. The object sensing component 12 panel shown in FIG. 2 has the first and second signal loops 16, 17 configured one within the other, however as described herein the signal loops 16, 17 can be arranged in any suitable topological arrangement such as side-by-side or one on top of the other. In the examples discussed herein the loops are substantially axisymmetric however it would be understood that in some embodiments any suitable arrangement of loops can be implemented.

Furthermore in some embodiments, where the object sensing component 12 is a display component or is a combined touch panel/display component, the touch sensor output connection can carry display information from the processor to the display element. For example in some embodiments the object sensing component 12 can be configured to display images within the touch sensitive area 18.

In some embodiments the first signal loop 17 at least partially surrounds the touch sensitive area 18. The first signal loop 17 is configured in some embodiments to be implemented within or on the touch panel component 12. Furthermore at least partially surrounding the first signal loop 17 is located the second signal loop 16 further implemented within or on the object sensing component 12 panel.

It would be understood that in some embodiments the object sensing component 12 is constructed from multiple layers. In such embodiments each signal loop can be implemented on the same layer or on different layers. The signal loops 16 and 17 can in some embodiments be implemented from any suitable conductive material. For example in some embodiments the signal loops can comprise a metallic film deposited over or on the object sensing component 12. In some other embodiments the signal loops can comprise a metallic film or foil layer sandwiched between layers forming the object sensing component 12. In some other embodiments the signal loops are formed from conductive foil or film structures adjacent to and formed during the manufacture of the object sensing component 12 panel. A foil or film layer in such embodiments can be applied uniformly across the object sensing component 12 panel and to create the touch sensitive area 18, the first signal loop 16 and the second signal loop 17 by removing an area of the foil or film using for example etching to create a suitable foil or film area.

With respect to FIG. 3a the object sensing component 12 panel is shown with respect to the external couplings to one of the signal loops. In the example shown in FIG. 3a the ends of the first signal loop 16 are coupled to a signal coupling 201 suitable for coupling or connecting the first signal loop 16 to components external to the object sensing component 12 panel. In some embodiments it would be understood that the signal coupling can be configured to operate as a signal input or signal output transferring signals between the signal loop and the components external to the object sensing component 12 panel. Therefore in some embodiments the signal coupling can provide an input to the signal loop for providing a current to be passed through the signal loop which would generate a magnetic field and provide an output configured to output current generated within the signal loop being sensitive to magnetic fields or alternating electrical fields.

With respect to FIG. 3b an example of the first signal loop 16 is shown in further detail. The first signal loop 16 as shown with respect to FIG. 3b can in some embodiments comprise more than a single loop or winding of conductive material, or wire. For example the first signal loop 16 shown in FIG. 3b shows a spiral arrangement of conductive loops or windings, however it would be understood that the windings can be arranged or configured in any suitable topology. For example in some embodiments the windings can, as shown in FIG. 3b be arranged on the same plane or in some embodiments at least some of the windings are on a separate plane for example similar to an air coil.

It will be understood that the number of windings may be greater than or fewer than five. Furthermore it will be understood that the number of windings used for the inner signal loop 17 and the outer signal loop 16 can be the same or differ according to some embodiments of the application.

Figure 3D:
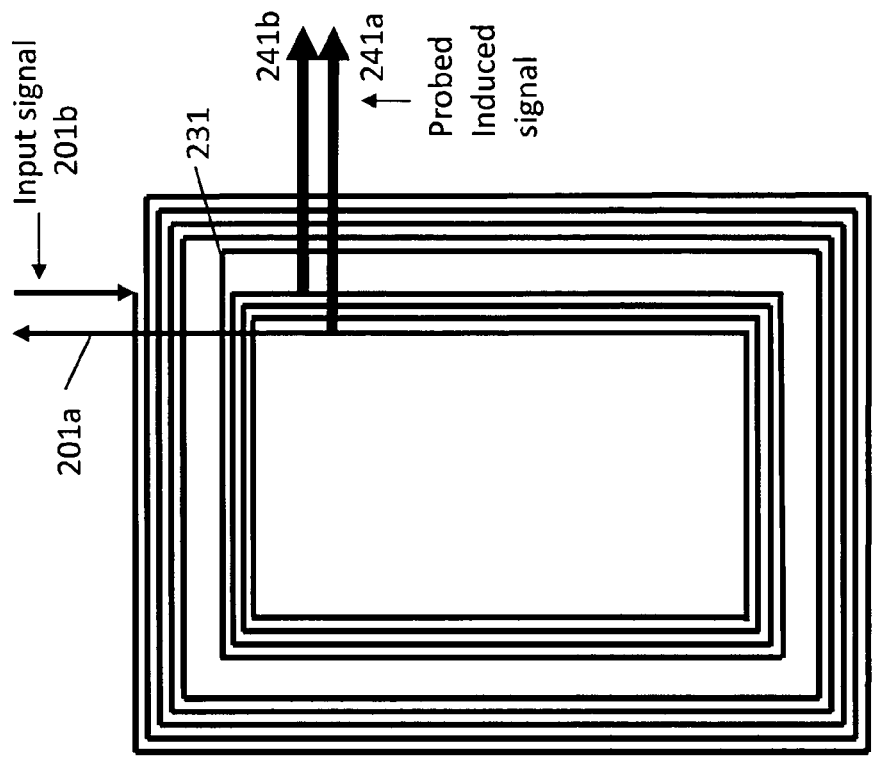
Figure 3C:
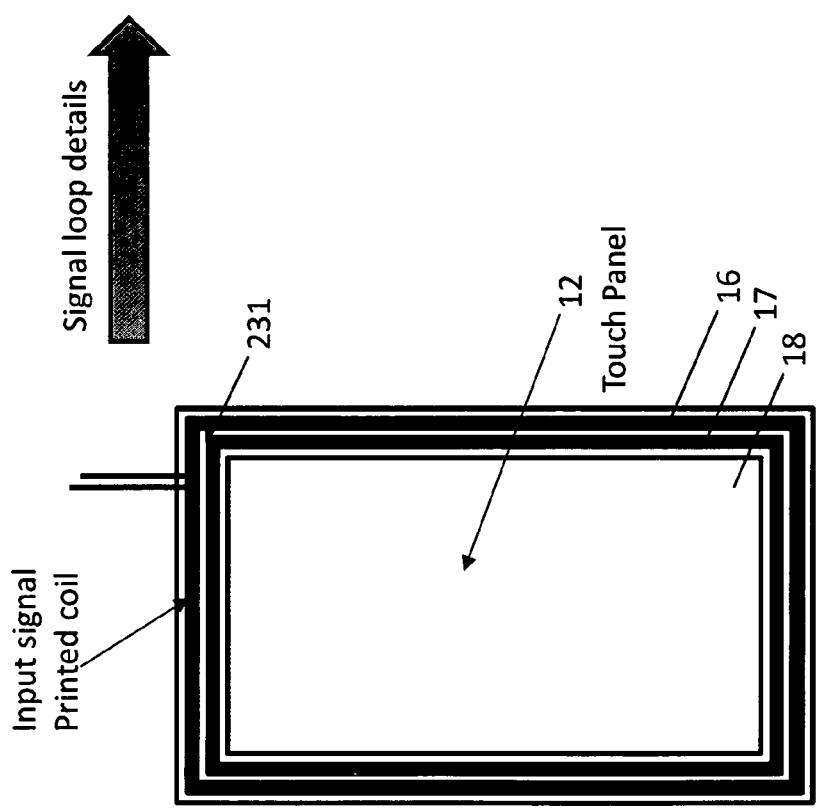

With respect to FIGS. 3c and 3d a further example of the object sensing component 12 and signal and reception loop configuration is shown. In the example shown in FIGS. 3c and 3d, the signal (or first) and reception (or second) loops are shown as being formed from a single loop configuration. This can be seen as having a (first) signal loop with a first input 201a and second input 201b coupled to the first and last of the signal loop windings and a (second) reception loop which has a first output 241a coupled to the first winding and a second output 241b coupled to a winding between the first and last winding. In other words the two loops (signal and reception) are at least partially overlapping or partially using the same windings with the partially overlapping windings coupled to the single use windings by a coupling 231.

In such embodiments it would be understood that the resonance frequency would differ from the completely separated loop configurations.

It would be understood that in some embodiments the single loop configuration has the reception loop with more windings than the signal loop.

Figure 4:
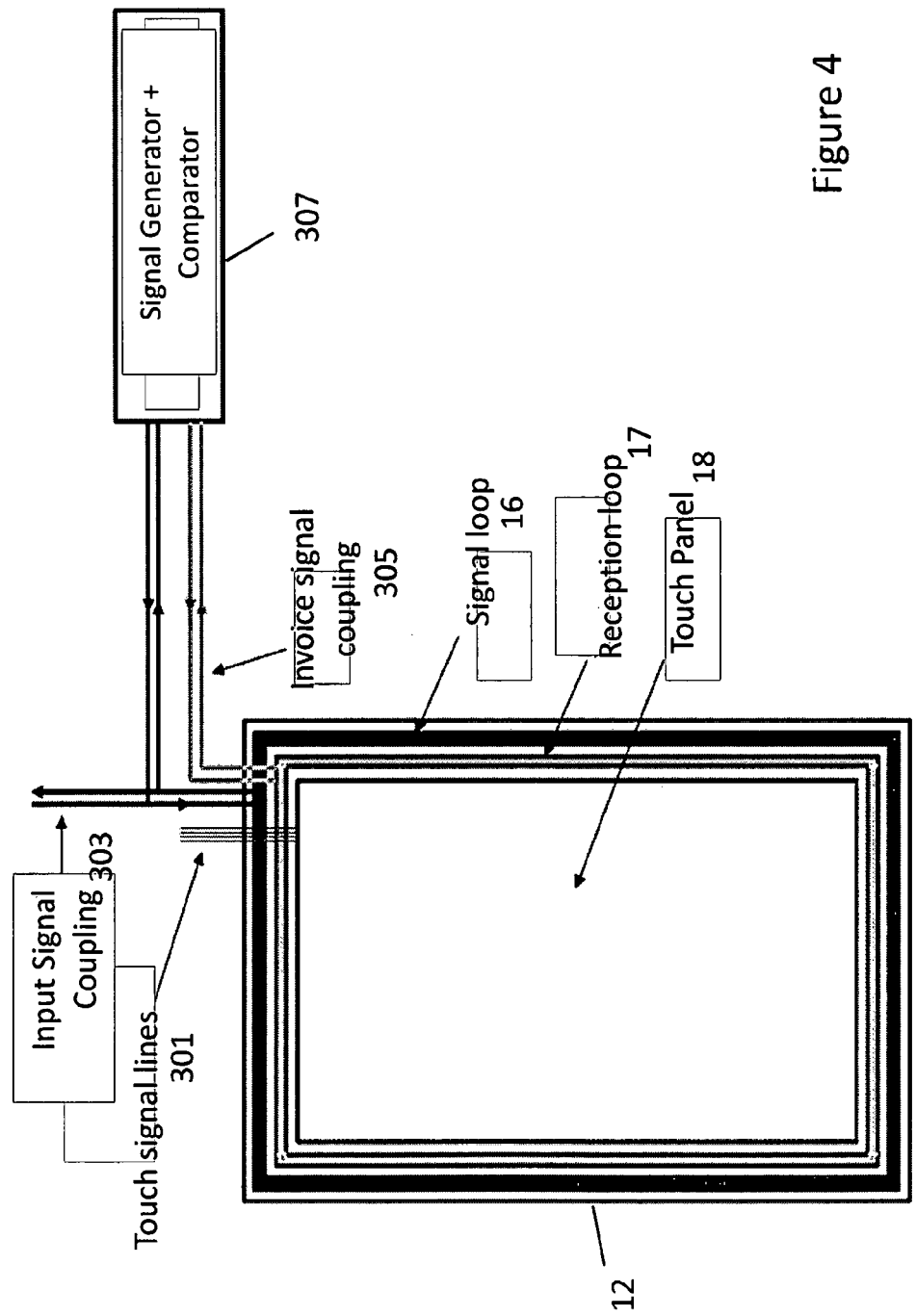
FIG. 4 shows schematically the object sensor component interface and signal generator and comparator according to some further embodiments.

With respect to FIG. 4 an example object sensing component 12 panel as coupled to further components of the apparatus is shown. The object sensing component 12 panel is shown comprising a first signal loop (signal coil) 16, a reception loop or second signal loop (reception coil) 17 and touch panel 18. The object sensing component 12 panel can furthermore be coupled to an input signal coupling 303 coupling the signal loop 16 with a signal generator and comparator 307, an induced signal coupling 305 coupling the reception loop 17 and the signal generator and comparator 307, and touch signal lines 301 configured in some embodiments to output touch panel user interface information to the processor. It would be understood that in some embodiments where the object sensing component 12 panel comprises only the signal loops 16 and 17 then only the input signal coupling and induced signal coupling is required to couple the signal loops to a signal generator and comparator.

Figure 5:
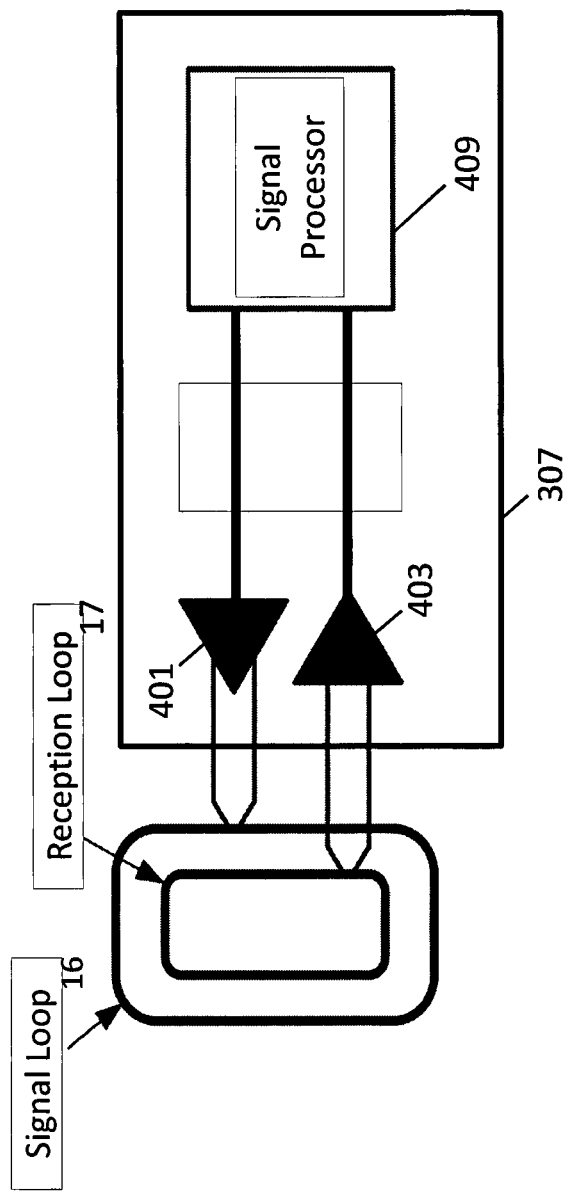
FIG. 5 shows schematically the signal generator and comparator in further detail according to some embodiments of the application.

With respect to FIG. 5 the signal generator and comparator 307 is shown in further detail. The signal generator and comparator 307 in some embodiments comprise a signal processor 409. The signal processor 409 is configured in some embodiments to generate digital signals to trigger the generation of magnetic fields by the (outer) signal loop 16.

In some embodiments the signal generator and comparator 307 can comprise an output power amplifier 401. The output power amplifier 401 can be configured to receive the output of the signal processor 409 and supply the signal loop 16 via the input signal coupling with a suitable current for generating a magnetic field or alternating electrical field.

The output power amplifier 401 can be any suitable amplifier implementation. The output power amplifier 401 is shown in FIG. 5 as being a single input, differential output amplifier however any suitable amplifier configuration can be used.

As discussed herein the first signal loop 16 current generates a magnetic field which induces a current in the second signal loop or reception loop 17.

In some embodiments the signal generator and comparator 307 can comprise an input amplifier 403. The input amplifier 403 can be configured to receive current or voltage signals generated within the reception loop (or inner loop) 17 and amplify the signal to a suitable level. The input power amplifier 403 can be any suitable amplifier configuration or technology, and is shown in FIG. 5 as a differential input supplied from the induced signal coupling 305 and a single output configuration.

The input amplifier 403 can in some embodiments be configured to receive the induced signal and output an amplified induced signal to the signal processor 409.

In some embodiments the signal processor 409 can be implemented by the processor of the apparatus 10 described herein or be a separate processor or component from the apparatus processor described herein.

In some embodiments the input amplifier and/or the output amplifier are configured to operate in the analogue domain and the signal generator and comparator 307 in some embodiments comprises an analogue-to-digital converter (ADC) and digital-to-analogue converter (DAC). The analogue-to-digital converter can be any suitable analogue-to-digital converter configuration or technology configured to input the analogue signal from the input amplifier 403 and output a suitable digital signal to the signal processor 409.

Similarly in some embodiments the digital-to-analogue (DAC) converter can be configured to receive the digital signal generated by the signal processor 409 and convert the digital signal into a suitable analogue signal formal. The digital-to-analogue converter can be configured in some embodiments to output the suitable analogue signal to the power amplifier. The DAC can be any suitable DAC implementation.

Although not shown in some embodiments the apparatus comprises an integrated hands free (IHF) speaker or transducer module configured to further receive a signal from the signal processor 409 and configured to output suitable audio signals. It would be understood that with respect to the application the use of the integrated hands free speaker or transducer module is to provide an output to the user indicating the detection of a metallic object. Similarly it would be understood that the apparatus can comprise and use any suitable user interface means to indicate to the user the detection of a metallic object (and in some embodiments the type of metallic object detected). For example the apparatus can comprise a vibra configured to vibrate the apparatus on detection of the metallic object, a light (for example from the display) configured to change intensity of colour, or the display displaying a pictorial or textual indicator of the detected object.

Figure 6:
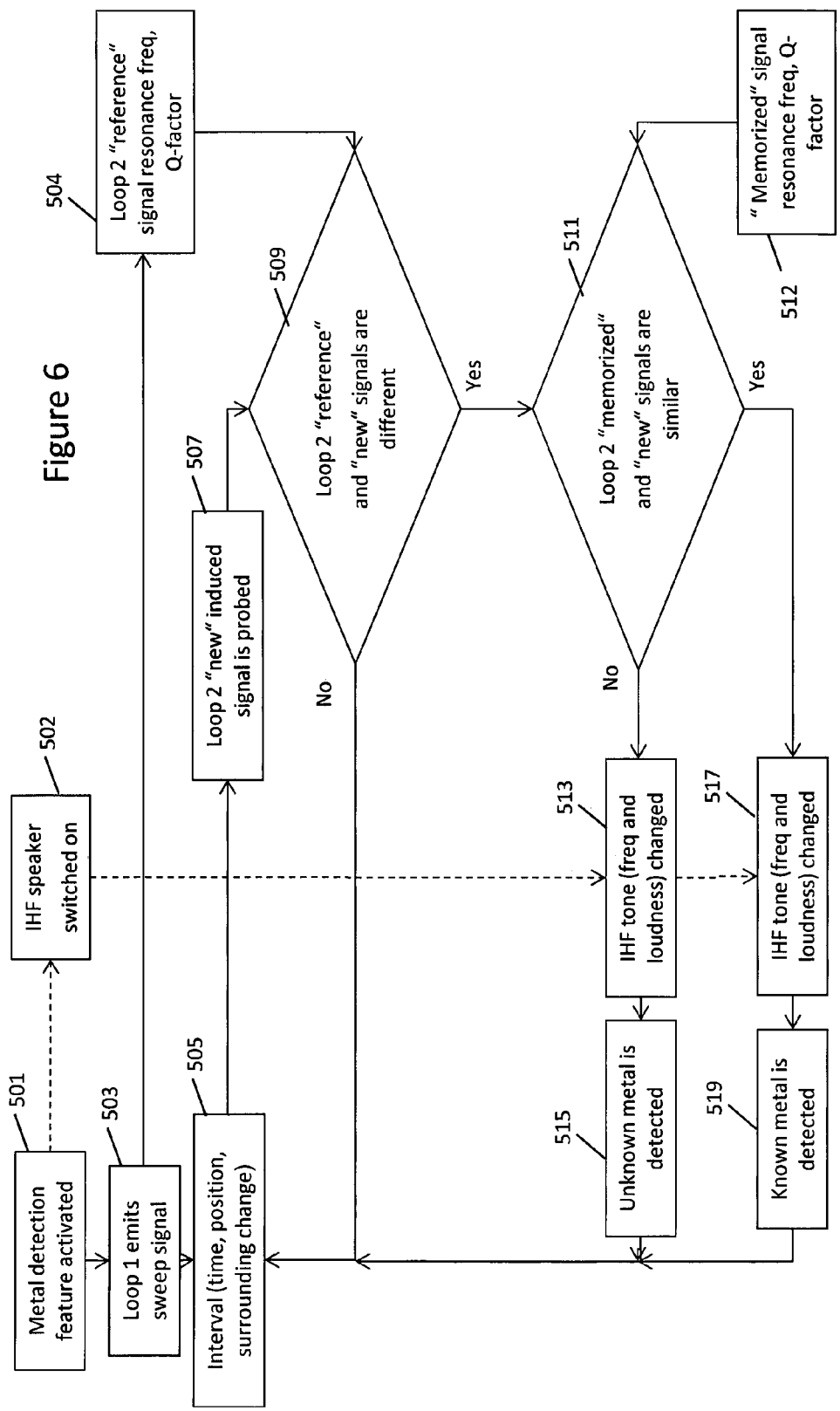
FIG. 6 shows schematically a flow diagram of the operation of the signal generator and comparator according to some embodiments of the application.

With respect to FIG. 6 the operation of the signal generator and comparator 307 shown in FIGS. 4 and 5 with respect to some embodiments of the application is shown.

In some embodiments the user interface can be configured to enable or activate a suitable application or program via the user interface to start a metal detection feature. In some other embodiments the activation of the metal detection feature can be configured to be either semi-automatic or automatic. In other words in some embodiments the metal detection application can be triggered either automatically based on some trigger event such as a timer or other sensor output.

The operation of activating the metal detection feature via the user interface is shown in FIG. 6 by step 501.

In some embodiments the activation of the metal detection feature can be configured to enable or activate the audio subsystem such as embodied by an integrated hands-free speaker (IHF). In some embodiments the integrated hands-free speaker is configured to generate an audible tone. The audible tone can for example indicate that a sensing operation is in progress, for example outputting a determined frequency tone or determined sequence of tones. In some embodiments the 'sensing tone' can be categorized by an audio signal of a particular frequency, length, periodicity, or loudness. It would be understood that in some embodiments the 'sensing tone' is dependent on the Q-factor of the system.

Furthermore the signal processor 409 having been activated via the user interface or metal detection program can be configured to generate a suitable sweep signal. The sweep signal can in some embodiments be a frequency modulated (FM), or amplitude modulated (AM) signal with a start and end value frequency. In some embodiments the start and end frequencies can be determined by the resonance of the apparatus. Furthermore in some embodiments the sweep signal can be a pulse signal (or interrupted wave signal). It would be understood that the resonance of the apparatus can be different from the resonance of the signal coils in isolation. For example any other metal part such as the touch screen, battery, cover of the apparatus can interfere and cause the resonance frequency of the signal loop to deviate from the expected two signal loop in free space resonance frequency.

The generation of signal loop sweep signals or pulse signals for generating magnetic fields is not described in further detail herein.

The signal processor 409 outputs the sweep signal to the output power amplifier 401. The output power amplifier 401 is further configured to amplify the sweep signal to generate a suitable drive signal to the outer loop or signal loop 16. The outer loop 16 or signal loop 16 is thus driven by the power amplifier 401 to emit a sweep signal in the form of a magnetic field or alternating electrical field, with suitable modulation.

The emission by the signal or outer loop of a sweep signal is shown in FIG. 6 by step 503.

While the apparatus 10 operates in free space, in other words away from any external induction interference the reception loop 17 senses the magnetic field or alternating electrical field generated by the signal loop 16 which generates by mutual induction a current in the reception loop 17 which can in some embodiments be passed to the input amplifier 403. The input amplifier 403 can further in some embodiments can be configured to output an amplified version of the inner loop received signal to the signal processor 409. The signal processor 409 can then be configured to store or record the 'free space' reception loop signal as a reference signal as generated by the reception loop. Furthermore in some embodiments as well as, or to replace, the 'free space' calibration a calibration can be also performed when the apparatus is over the ground.

In some embodiments the user or operator of the apparatus can generate the 'reference' signal as part of a calibration cycle or operation. However in some embodiments it would be understood that the generation or storage of the 'free space' reference signal can be performed during the apparatus manufacturing and testing operations.

The storing of a reference signal from the reception loop 17 is shown in FIG. 6 by step 504.

The apparatus 10 can be operated so that after a predetermined interval a further sweep is performed. In some embodiments the interval is a time period and/or a distance moved by the apparatus.

The interval is shown in FIG. 6 by step 505.

Following the interval the further sweep is performed. Where for example after a period the apparatus is moved towards a metal object or where a metal object is moved towards the signal and reception loops then the metal object neighbouring the loops interferes with the mutual magnetic coupling between the signal loop 16 and the reception loop 17. This interference would be reflected by a change in signal generated by the reception loop based on the sweep signal from the signal loop. Where there is no neighbouring material then the sweep signal would not change from the 'reference' signal. The reception loop signal, being passed via the input amplifier 403 is received by the signal processor 409. The generated signal in the second loop can in some embodiments be considered to define a resonance profile signal with respect to the swept signal input to the first loop. The resonance profile can be identified or defined with respect to at least one resonance frequency and in some embodiments at least one associated resonance frequency amplitude and at least one associated resonance frequency quality factor.

The generation of a 'new' induced signal is shown in FIG. 6 by step 507.

Figures 8A, 8B:
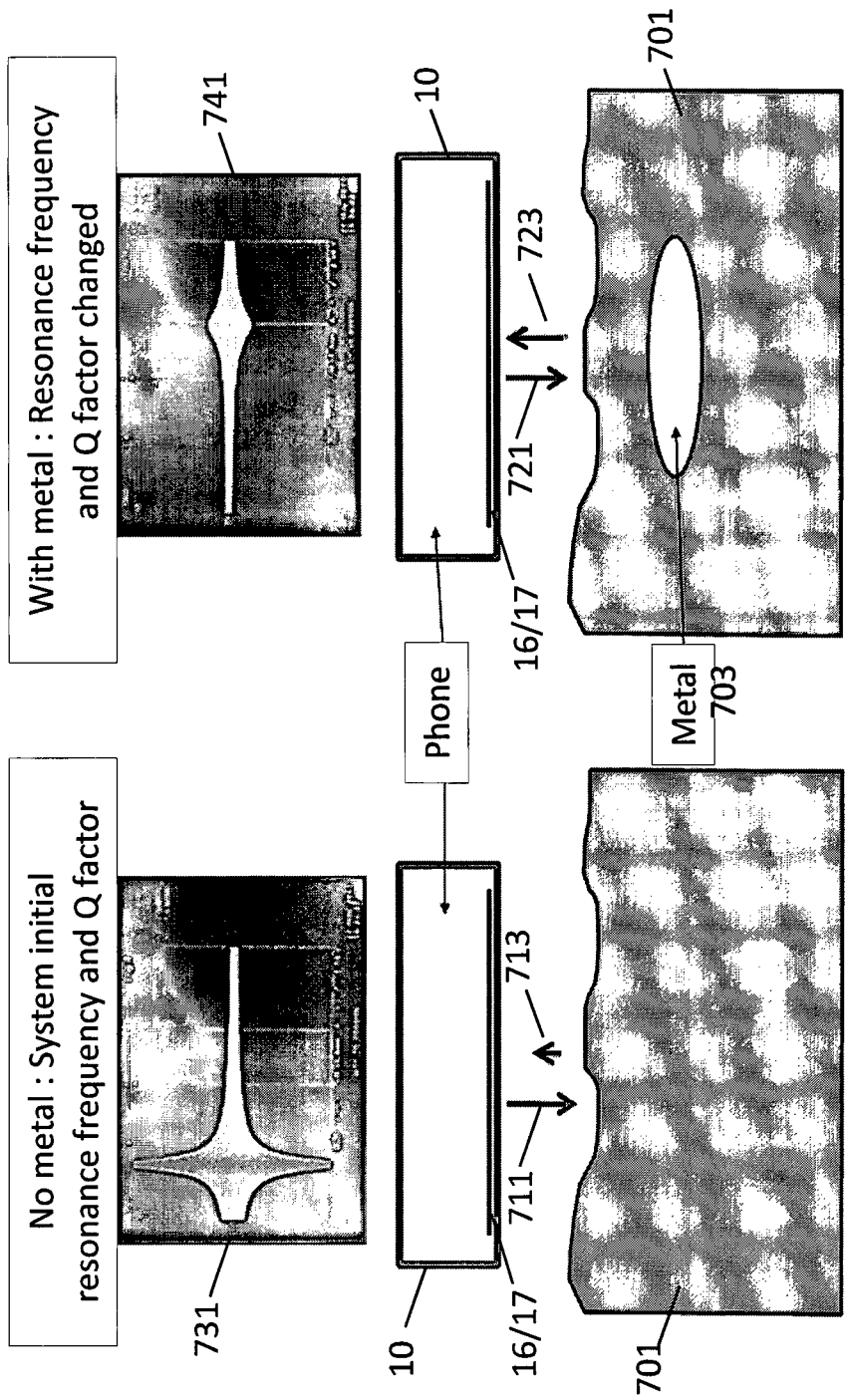
FIGS. 8a and 8b shows schematically example metal detection using the printed coil sensor according to some embodiments of the application.

An example 'reference' and 'new' signal is shown with respect to FIGS. 8a and 8b respectively.

With respect to FIGS. 8a and 8b example resonant signals are shown. With respect to FIG. 8a an apparatus 10 with signal and reception loops 16/17 are located close to the ground 701 or other surface (i.e. a reference signal is returned). The signal loop as described herein is configured to generate a magnetic field represented by arrow 711 which is interfered by the object 701 causing induction 713 in the reception loop. This is because some types of surface can have a natural conductivity and which in response to the magnetic field can generate some interference shown by the induction 713. Thus in some embodiments the reference or calibration operation can be performed over the ground and not in free space to take into account the natural conductivity of the ground. It would be understood that the conductivity of the ground or surface depends on the composition of the ground or surface, for example mineral content, the formation of the material, whether the ground is largely crystalline or particulate in nature for example. The signal sweep, the signal frequency will generate an initial resonance frequency and Q-factor caused by the mutual induction between the signal and reception loop which is shown pictorially by the oscilloscope trace 731.

With respect to FIG. 8b the same apparatus 10 as shown in FIG. 8a is shown with the introduction of a metal object 703 within the object or surface 701 i.e. a 'new' signal is shown. The metal object 703 interferes with the generated magnetic field 721 creating a magnetic field 723 which is detected at the reception loop and which has a different resonant frequency and Q-factor as shown by the oscilloscope trace.

The signal processor 409 can therefore be configured in some embodiments to compare the signals received via the reception loop and determine whether there is a difference between the 'reference' and the 'new' induced signals.

Where the 'reference' and the 'new' induced signals differ then the signal generator and comparator or signal processor can indicate that a metallic object is close.

The operation of comparing the 'reference' to the 'new' signal is shown in FIG. 6 by step 509.

Where the 'reference' and the 'new' signals are similar, in other words there is no or substantially little difference between the sweeps then the signal processor 409 can be configured to perform a metal object not detected operation. For example the signal processor can be configured in some embodiments to control the audio subsystem so that the integrated hands-free audio signal output is maintained in tone, signal periodicity or volume.

The operation then in some embodiments can pass back to step 507 via step 505 where after a further interval a 'new' induced signal is generated by performing a further sweep. The 'new' signal can be generated after an interval of a determined amount of time, distance moved or manually by the user in some embodiments.

Furthermore the detection of a 'reference' and 'new' signal similarity can be configured to provide the processor with an indicator which then enables the processor to output a visual indication that no metal has been detected.

In some embodiments the difference between 'reference' and 'new' signals can be further analysed to determine for example the type of metal in the object, the composition of metals in the object, or the location or orientation of the metal object or objects.

For example in some embodiments the 'new' signal can be compared against a metal reference or memorized signal.

In some embodiment the signal processor can retrieve a memorized signal from a memory. The memorized signal in some embodiments can be a suitable stored component of the signal for example the memorized signal can comprise a resonance frequency and Q-factor associated with a known metal.

The memorized signal (metal reference signal) can in some embodiments be a reference signal stored within the apparatus memory where during the apparatus manufacture and testing operations the loops were calibrated on a series of metal types. In some embodiments the memorized signal (metal reference signal) is a predetermined signal stored in memory. In the following example one memorized signal is retrieved (and compared against the 'new' signal). However it would be understood that in some embodiments a range of memorized signals can be retrieved and compared to attempt to match the detected metal against one of the retrieved memorized metals.

The operation of retrieving a memorized signal is shown in FIG. 6 by step 512.

Where the loop 'reference' and the 'new' signal are different then the signal processor 409 can in some embodiments search the retrieved memorized signals to determine whether a match is made between the 'new' signal and the memorized signal, in other words whether the 'new' signal and the memorized signal is similar.

The operation of comparing between the memorized and new signals is shown in FIG. 6 by step 511.

Where the 'memorized' and 'new' signals are similar, in other words a match or near match is made between the 'new' signal and a signal associated with a known metal the IHF is configured to output a signal which identifies that a known metal is detected. For example in some embodiments the known metal has an associated audio tone which is output by the IHF. In some embodiments it would be understood that the IHF can output a specific frequency, or loudness associated with the known metal being detected.

The operation of outputting an IHF signal associated with the known metal is shown in FIG. 6 by step 517.

In some embodiments any suitable user interface output can be used to indicate the known metal detection. For example the display can be used to output a textual, pictorial or icon of the known metal.

The operation of detecting a known metal is shown in FIG. 6 by step 519.

In some embodiments following the detection of a known metal object the signal processor operation passes to step 505, and performs a further interval operation.

Where the 'memorized' and 'new' signals are not similar, in other words no match is made between the 'new' signal and a signal associated with a known metal the IHF is configured to output a signal which identifies that an unknown metal is detected. For example in some embodiments the detection of an unknown metal has an associated audio tone which is output by the IHF. In some embodiments it would be understood that the IHF can output a specific frequency, or loudness associated with the unknown metal being detected.

The operation of outputting an IHF signal associated with the unknown metal being detected is shown in FIG. 6 by step 513.

In some embodiments any suitable user interface output can be used to indicate the detection of the unknown metal object. For example the display can be used to output a textual, pictorial or icon of the detection of the unknown metal.

The operation of detecting an unknown metal is shown in FIG. 6 by step 515.

In some embodiments following the detection of an unknown metal object the signal processor operation passes to step 505, and performs a further interval operation.

In some embodiments the signal processor 409 is not concerned in determining or detecting what type of metal has been detected only that a metal object is present and therefore in some embodiments can be configured to generate a 'metal detected' signal to indicate that a metal object neighbours the signal/reception signal loops.

In such embodiments the metal object detected operation can comprises the signal processor 409 being configured to control the audio subsystem to change the acoustic signal output by the IHF speaker. In such embodiments the audio subsystem can be configured to change the IHF output signal (tone frequency, pulse period, volume etc) dependant on the detection of the metal object. The change can in some embodiments be further dependent on the type of metal detected, the change of resonance frequency, the change in Q factor of the resonance etc.

Furthermore in some embodiments the apparatus can be configured to output a visual display of the operation of detecting the metal object. For example the apparatus display can brighten or change colour to represent the detected metal.

This detection of the metal object causing a change in resonant frequency and Q-factor can furthermore in some embodiments be used by an apparatus as a form of user interface input.

For example a mobile phone should not be used in a held mode of operation while operating a vehicle. Often vehicles are equipped with 'car kit' which features a Bluetooth transceiver coupled to the vehicles audio system. The mobile device when operated within the vehicle can via the user interface enable the Bluetooth transceiver within the device to communicate with the car kit Bluetooth transceiver enabling the mobile device to be used whilst the user is operating the vehicle.

Figure 9:
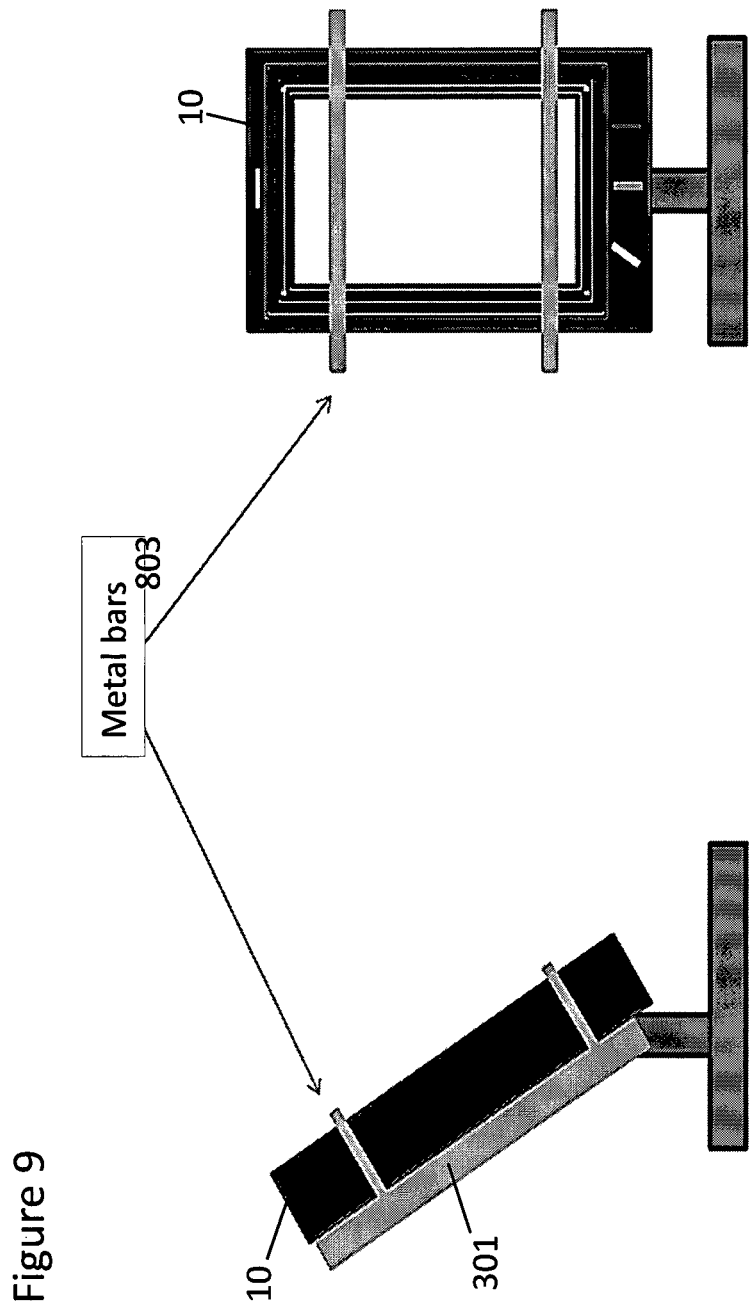
FIG. 9 shows schematically a further example user interface input use for embodiments of the application with respect to user interface docking stations.

As shown in FIG. 9 a mobile phone or mobile apparatus holder 801 comprising metal clips or bars 803 holding the apparatus 10 in place can be detected by the reception loop 17 when the mobile apparatus is located correctly in the holder.

The detection by the reception loop 17 can for example be configured to enable the apparatus 10 and in particular the processor of the apparatus to enable a specific mode of operation. For example should the holder 801 be part of a car-kit then on detecting the metal bars 803 when the apparatus is inserted into the car-kit the processor for the apparatus can configure the apparatus to operate in to a 'car' mode. For example in such a car-mode the Bluetooth interface can be enabled, and coupled to the car-kit Bluetooth interface to enable hands-free operation of the apparatus. Furthermore the apparatus can be configured to interface with the car kit electronics to enable control of audio functions of the mobile device from the car, such as from the steering wheel controls to enable the apparatus 10 to output audio files to be listened to via the vehicle audio system.

Similar user interface interaction can occur for example where the apparatus is inserted into a suitably designed audio-port in a hi-fi where the detection of metallic indicators, such as metallic bars or strips and the detection of specific combinations of metals similarly enable the apparatus to interact with the hi-fi.

In some further embodiments a particular metallic object such as a bracelet, ring can be configured to trigger a particular phone call for the person associated with the object. For example a wedding ring could trigger a phone call to the partner of the user.

With respect to FIG. 7 a further configuration of the apparatus and an example practical use of the metal detection operation with respect to user interface operation is described in further detail. In such an example the object sensing component 12 panel is configured with a reception loop 17 which comprises sub-loops distributed over the panel area. Thus for example as shown in FIG. 7 the reception loop 17 comprises a first sub-loop 17a configured to cover the 'top left' quadrant, a second sub-loop 17b configured to cover the 'bottom left' quadrant, a third sub-loop 17c configured to cover the 'bottom right' quadrant and a fourth sub-loop 17d configured to cover the 'top right' quadrant. The arrangement of the sub-loop reception loops is such that they can be configured to determine where the metal object is in relation to the object sensing component 12 panel. A processor can be configured to receive the sub-loop reception loop signals over successive sweeps of each sub-loop and in some embodiments determine relative motion of a metal object with respect to the object sensing component 12 panel and the direction of motion of the metal object. A practical use of this in some embodiments would be as an user interface input where for example a metallic object, for example a pen 601 is moved 'up' 603 the object sensing panel area but not touching the panel can cause a change in the apparatus. In other words the signal processor can detect or determine when the induced signal caused by the proximity of the metal object in the 'bottom' quadrants decreases and the induced signal caused by the proximity of the metal object in the 'upper' quadrants increases. This change can in some embodiments for example be used to control a volume level output whereby as the object is moved 'upwards' the volume is increased 605 and as the object is moved 'downwards' the volume is decreased. It would be understood that the number of detected areas can be more than or fewer than four, and be any suitable arrangement of areas or regions and that the sensed metallic object can be used as any suitable user interface input.

Figure 10:
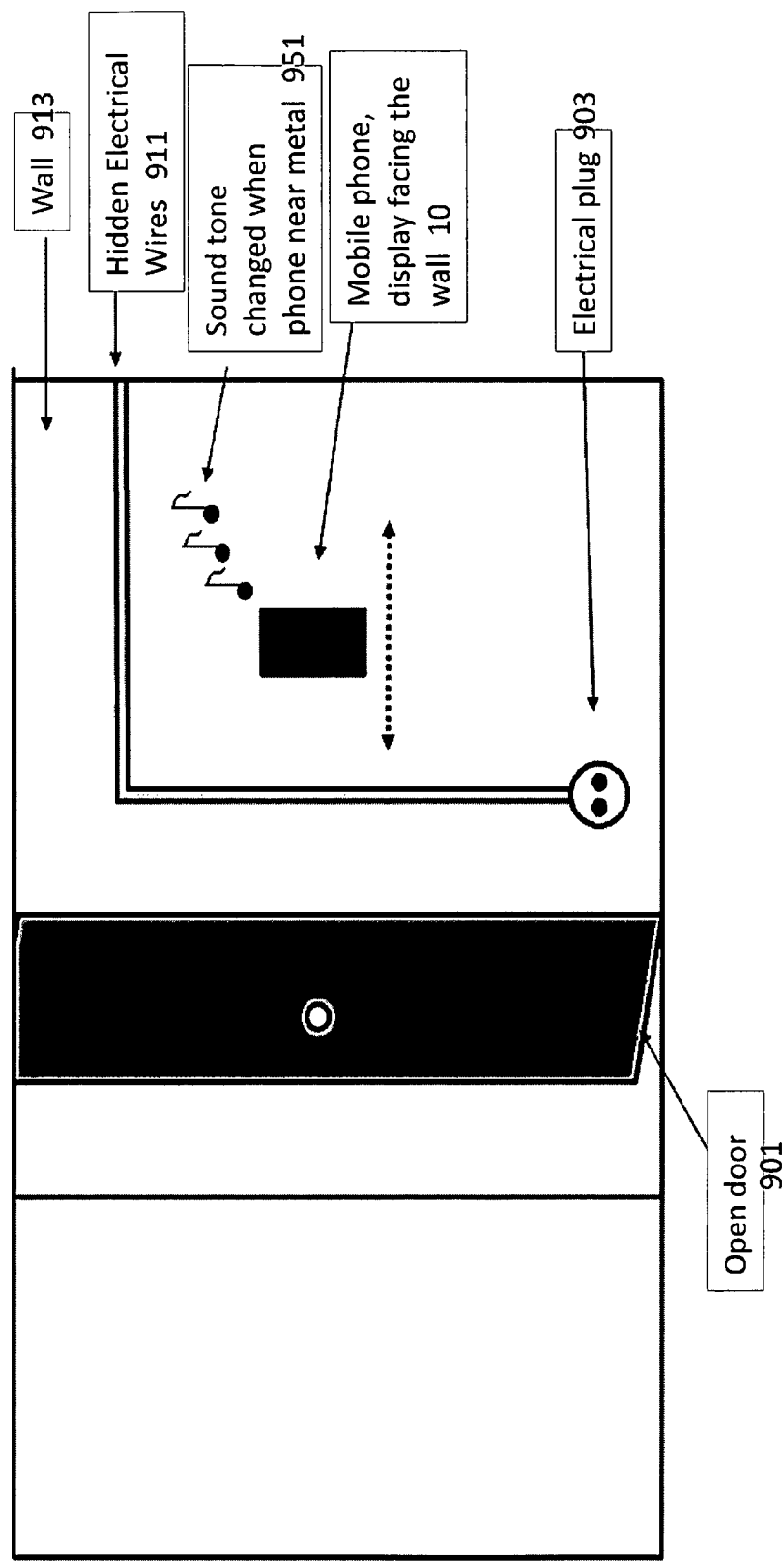
FIG. 10 shows schematically a further example use for embodiments of the application with respect to cable detection.

With respect to FIG. 10 a further example use of the apparatus according to some embodiments is shown wherein the apparatus can be configured to operate as a cable or wire detector. The apparatus 10 can for example as shown in FIG. 10 be orientated such that the display faces the wall 913 as the apparatus is moved across the wall any hidden electrical wire 911 or cable or metal object within the wall can be detected as the magnetic field coupling between the signal and reception loops is interfered with by the metal. In some embodiments an approximate location of the metallic object can be displayed by the apparatus where the visual display brightens sufficiently on determination of metal to 'light' the wall over the hidden metal object.

Figure 11B:
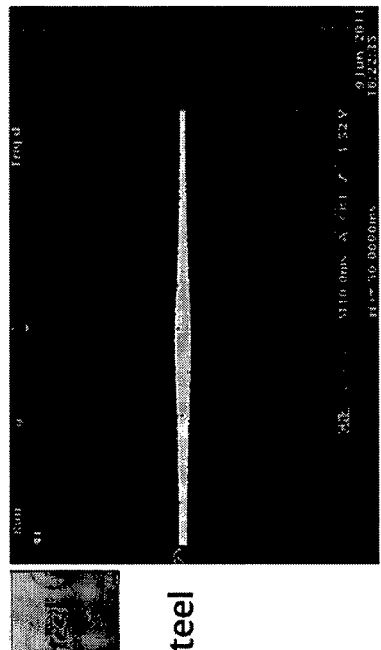
FIGS. 11a to 11d show example demonstration outputs for various material detection samples.
Figure 11A:
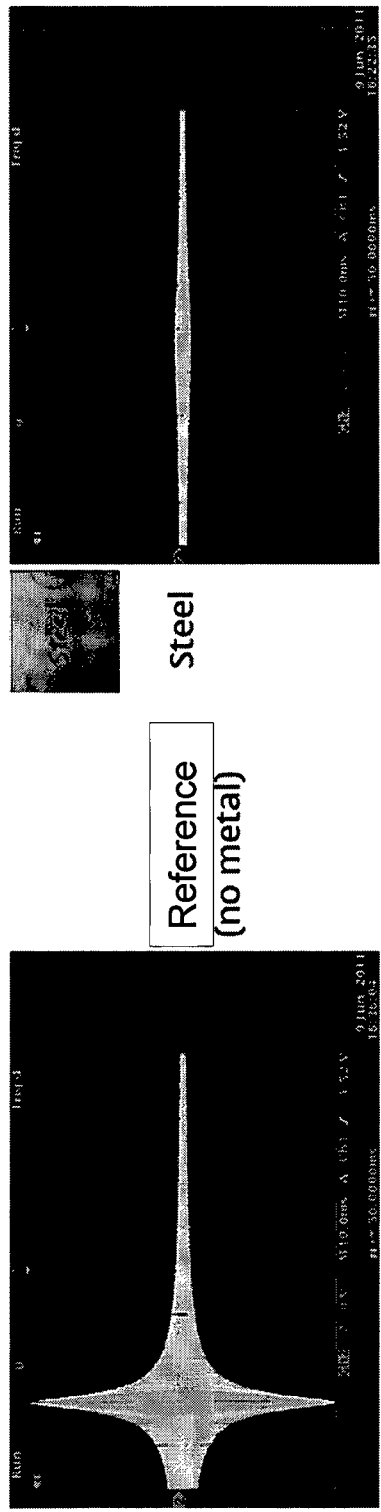

With respect to FIGS. 11a to 11d a sequence of induction loop signal profiles between 1 MHz and 2 MHz are shown for a range of neighbouring objects. These outputs show that each type of metal can in some embodiments induce a different output signal profile. In the demonstration examples all of the test objects had similar dimensions, and only the material was different. Thus for example a free space, reference, or no metal signal profile as shown in FIG. 11a shows the loop system resonance frequency of 1.2 MHz and with a Q-factor.

With reference to FIG. 11b a signal profile showing the proximity of a steel object flattens the signal profile (lowering the Q-factor) and showing a slight peak at approximately 1.5 MHz.

Figure 11D:
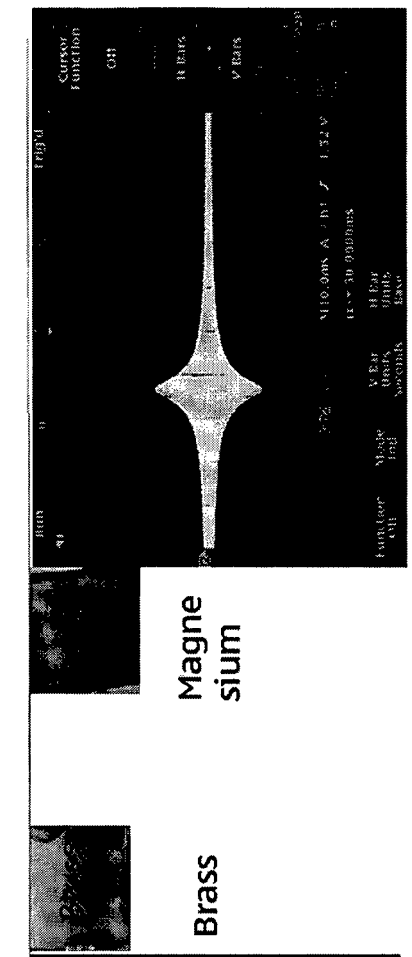
Figure 11C:
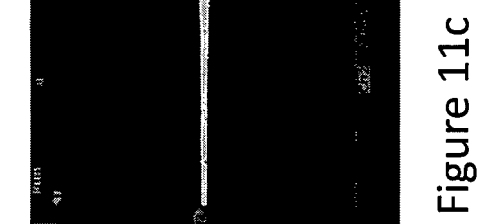

With respect to FIG. 11c a signal profile showing the proximity of a brass object shows the resonant frequency moving to a higher frequency.

With respect to FIG. 11d a signal profile showing the proximity of a magnesium object shows the resonant frequency moves to a higher frequency than when operated in free space but not as high as either steel or brass resonant frequencies but the profile has a greater Q-factor.

Figure 12:
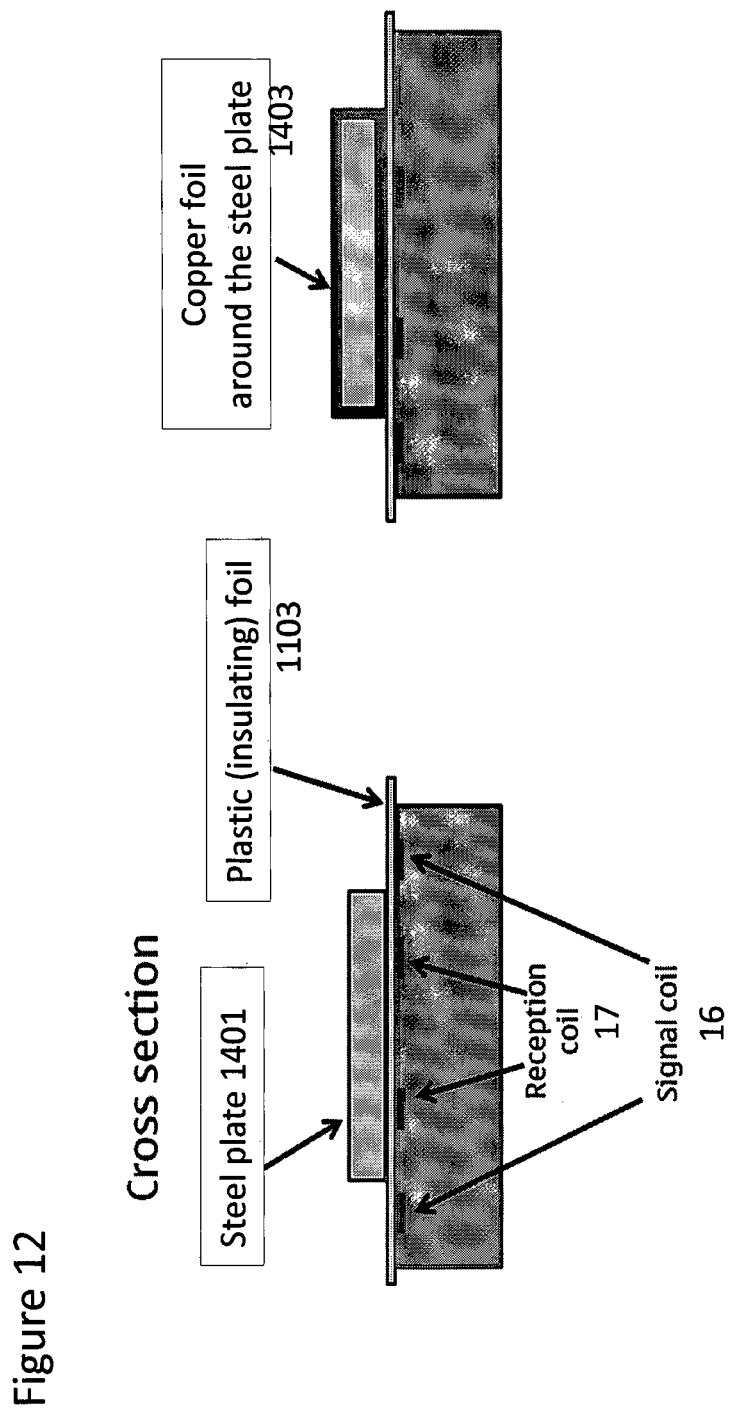
FIG. 12 show example complex material detection samples.

As described herein these signal profiles can be configured to enable the apparatus to detect not only a metal object but the composition of the object. For example with respect to FIGS. 12 and 13 an example of composite metal object detection is shown. With respect to FIG. 12 a cross section of a first object, a steel plate 1401 in contact with the plastic insulating foil 1103 overlying the reception loop 17 and signal loop 16 is shown.

Figure 13:
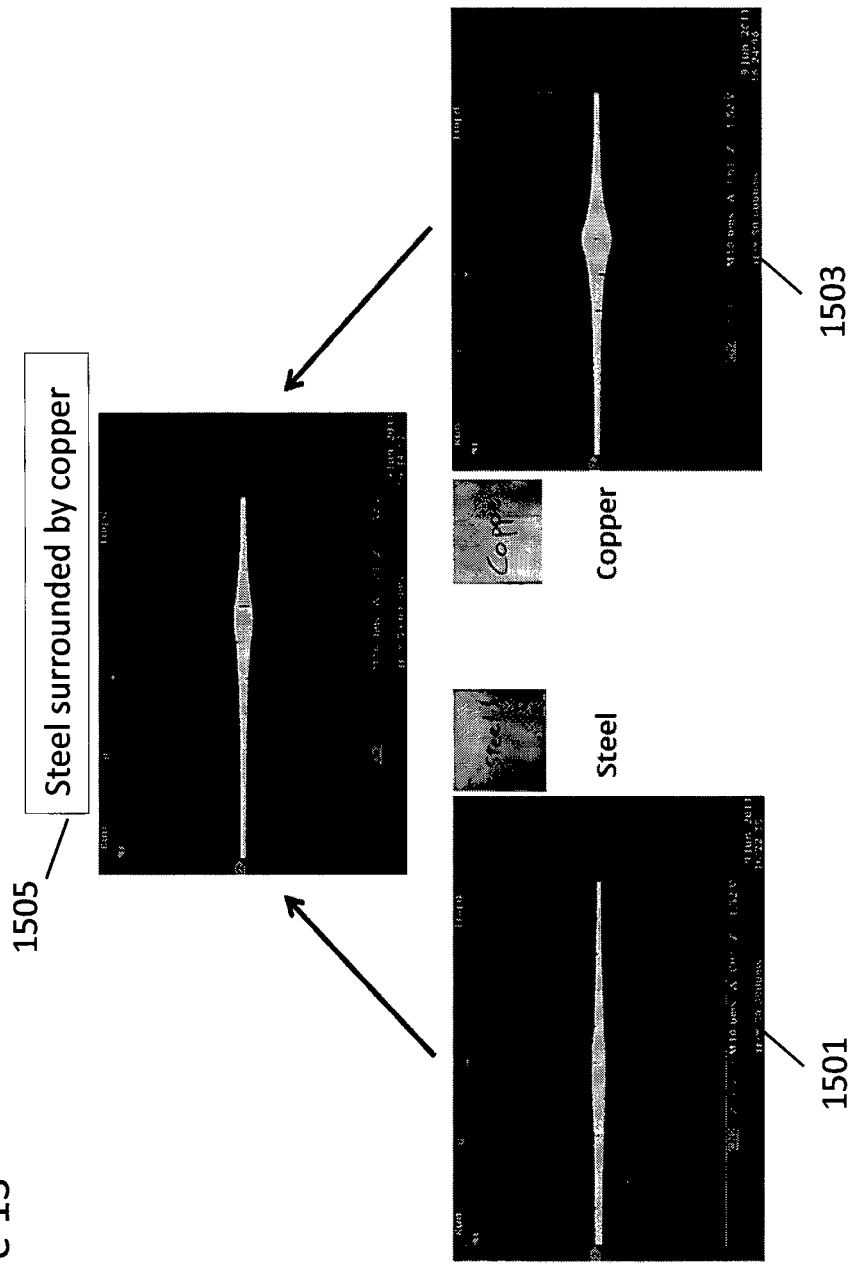
FIG. 13 shows show example demonstration outputs for the example complex material detection sample.

The steel plate 1401 overlying the reception loop and signal loop produces a signal profile shown in FIG. 13 by the steel signal profile 1501.

A copper object placed over or in contact with the plastic insulating foil 1103 would be configured to generate a signal profile of a copper object 1503 as shown in FIG. 13.

However, when a copper foil surrounding a steel plate object 1403 is located over the reception and signal loops, a combination of the two signal profiles is shown 1505.

Thus in some embodiments it is possible to determine whether the object is pure, or mixed.

It shall be appreciated that the term electronic device and user equipment is intended to cover any suitable type of wireless user equipment, such as mobile telephones, portable data processing devices or portable web browsers.

In general, the various embodiments of the invention may be implemented in hardware or special purpose circuits, software, logic or any combination thereof. For example, some aspects may be implemented in hardware, while other aspects may be implemented in firmware or software which may be executed by a controller, microprocessor or other computing device, although the invention is not limited thereto. While various aspects of the invention may be illustrated and described as block diagrams, flow charts, or using some other pictorial representation, it is well understood that these blocks, apparatus, systems, techniques or methods described herein may be implemented in, as non-limiting examples, hardware, software, firmware, special purpose circuits or logic, general purpose hardware or controller or other computing devices, or some combination thereof.

Thus in at least one of the embodiments there is an apparatus comprising a display component comprising at least one display part and an electrically conductive part electrically isolated from the at least one display part. In at least one of these embodiments the conductive part is adjacent to and at least partially surrounds the at least one display part. Furthermore the conductive part is configured to form an induction coil in at least one of these embodiments. The induction coil is in at least one of the embodiments a single loop of conductive material, and in at least a further embodiment at least two loops of conductive material, wherein the at least two loops of conductive material are at least one of: a single layer comprising at least two loops of conductive material; and at least two serially connected layers, each layer comprising at least one loop of conductive material.

Furthermore in such embodiments at least one may further comprise at least one electrostatic discharge component, the conductive part being configured to be connected to the at least one electrostatic discharge component, and the conductive part and electrostatic discharge component configured to provide a discharge path to protect the display part.

Also in at least one of these embodiments the apparatus may further comprise a radio frequency transceiver, the conductive part being configured to be connected to the radio frequency transceiver, and the conductive part configured to provide an antenna path for the radio frequency transceiver.

Similarly in at least one of these embodiments the apparatus may further comprise a power management unit, the conductive part being configured to be connected to the power management unit, wherein the conductive part is configured to magnetically transfer power between the apparatus and at least one further apparatus.

The apparatus in at least one of the embodiments may further comprise an audio signal generator, the conductive part being connected to the audio signal generator, wherein the conductive part is configured to magnetically transfer the output of the audio signal generator to at least one further apparatus.

As described above thus in at least one of the embodiments the conductive part is configured to generate a hearing aid compatible magnetic field.

Also where the display component comprises at least one layer the at least one display part and the electrically conductive part are located on or in at least one of the at least one layer.

The display component as described above comprises a touch interface display and the display part comprises at least one touch sensitive part.

The embodiments of this invention may be implemented by computer software executable by a data processor of the mobile device, such as in the processor entity, or by hardware, or by a combination of software and hardware. Further in this regard it should be noted that any blocks of the logic flow as in the Figures may represent program steps, or interconnected logic circuits, blocks and functions, or a combination of program steps and logic circuits, blocks and functions. The software may be stored on such physical media as memory chips, or memory blocks implemented within the processor, magnetic media such as hard disk or floppy disks, and optical media such as for example DVD and the data variants thereof, CD.

Hence in at least one embodiment there is provided a computer-readable medium encoded with instructions that, when executed by a computer perform: presenting visual information with a display; and controlling an induction coil electrically isolated but located on or in the display.

The memory may be of any type suitable to the local technical environment and may be implemented using any suitable data storage technology, such as semiconductor-based memory devices, magnetic memory devices and systems, optical memory devices and systems, fixed memory and removable memory. The data processors may be of any type suitable to the local technical environment, and may include one or more of general purpose computers, special purpose computers, microprocessors, digital signal processors (DSPs), application specific integrated circuits (ASIC), gate level circuits (such as field programmable gate array—FPGA circuits) and processors based on multi-core processor architecture, as non-limiting examples.

Embodiments of the inventions may be practiced in various components such as integrated circuit modules. The design of integrated circuits is by and large a highly automated process. Complex and powerful software tools are available for converting a logic level design into a semiconductor circuit design ready to be etched and formed on a semiconductor substrate.

Programs, such as those provided by Synopsys, Inc. of Mountain View, Calif. and Cadence Design, of San Jose, Calif. automatically route conductors and locate components on a semiconductor chip using well established rules of design as well as libraries of pre-stored design modules. Once the design for a semiconductor circuit has been completed, the resultant design, in a standardized electronic format (e.g., Opus, GDSII, or the like) may be transmitted to a semiconductor fabrication facility or "fab" for fabrication.

As used in this application, the term 'circuitry' refers to all of the following:

(a) hardware-only circuit implementations (such as implementations in only analog and/or digital circuitry) and
(b) to combinations of circuits and software (and/or firmware), such as: (i) to a combination of processor(s) or (ii) to portions of processor(s)/software (including digital signal processor(s)), software, and memory(ies) that work together to cause an apparatus, such as a mobile phone or server, to perform various functions and
(c) to circuits, such as a microprocessor(s) or a portion of a microprocessor(s), that require software or firmware for operation, even if the software or firmware is not physically present.

This definition of 'circuitry' applies to all uses of this term in this application, including any claims. As a further example, as used in this application, the term 'circuitry' would also cover an implementation of merely a processor (or multiple processors) or portion of a processor and its (or their) accompanying software and/or firmware. The term 'circuitry' would also cover, for example and if applicable to the particular claim element, a baseband integrated circuit or applications processor integrated circuit for a mobile phone or similar integrated circuit in server, a cellular network device, or other network device.

The foregoing description has provided by way of exemplary and non-limiting examples a full and informative description of the exemplary embodiment of this invention. However, various modifications and adaptations may become apparent to those skilled in the relevant arts in view of the foregoing description, when read in conjunction with the accompanying drawings and the appended claims.

However, all such and similar modifications of the teachings of this invention will still fall within the scope of this invention as defined in the appended claims.

The invention claimed is:

1. An apparatus comprising:
  at least one first signal loop configured to receive a first signal;
  at least one second signal loop magnetically coupled with the at least one first signal loop configured to generate a second signal based on induction when the at least one first signal loop receives the first signal and is magnetically coupled with the at least one second signal loop; and
  a signal processor configured to monitor the second signal and determine a presence of at least one metal object dependent on induction interference of the at least one metal object on the second signal when the at least one first signal loop is magnetically coupled with the at least one second signal loop.

2. The apparatus as claimed in claim 1, wherein the at least one first signal loop comprises a conductive material adjacent to and at least partially surrounding an apparatus display.

3. The apparatus as claimed in claim 1, wherein the at least one second signal loop comprises a conductive material adjacent to and at least partially surrounding an apparatus display.

4. The apparatus as claimed in claim 1, wherein at least one of the at least one first signal loop and the at least one second signal loop are formed from a part of the other of the at least one second signal loop and the at least one first signal loop respectively.

5. The apparatus as claimed in claim 1, wherein the first signal comprises at least one of:
  an amplitude modulated signal;
  a frequency modulated signal; and
  an interrupted wave modulated signal.

6. The apparatus as claimed in claim 1, wherein the first signal comprises a swept signal having a first frequency range.

7. The apparatus as claimed in claim 1, wherein the second signal comprises a resonance profile signal and the resonance profile signal comprises at least one of:
   at least one resonance frequency;
   at least one associated resonance frequency amplitude; and
   at least one associated resonance frequency quality factor.

8. The apparatus as claimed in claim 7, wherein the signal processor is configured to determine a difference between a reference resonance profile signal and the resonance profile signal to determine the presence of at least one metallic object.

9. The apparatus as claimed in claim 8, further comprising a memory configured to store the reference resonance profile signal.

10. The apparatus as claimed in claim 7, further comprising a memory configured to include at least one memorized resonance profile signal associated with an identified metal; wherein the signal processor is configured to determine the at least one metallic object is the identified metal when the resonance profile signal at least partially matches the at least one memorized resonance profile signal.

11. The apparatus as claimed in claim 1, wherein the signal processor is further configured to determine dependent on the second signal at least one of:
   a composition of metals in the object;
   a location of the metal object; and
   an orientation of the metal object.

12. The apparatus as claimed in claim 1, wherein the at least one second signal loop comprises at least two second signal loops, each of the at least two second signal loops located or orientated differently to each other, such that the the signal processor is configured to determine a motion of the at least one metal object dependent on the second signal from each of the at least two second signal loops.

13. The apparatus as claimed in claim 1, further comprising a controller configured to control the apparatus dependent on determining the presence of the at least one metal object.

14. The apparatus as claimed in claim 13, further comprising a user interface output wherein the controller is configured to control the user interface output dependent on the determining at least one of the presence of the at least one metal object, a relative motion of the at least one metal object, and a proximity of the at least one metal object.

15. The apparatus as claimed in claim 14, wherein the user interface output comprises at least one of:
   a display configured to change dependent on the determining the presence of the at least one metal object;
   a speaker configured to output a tone dependent on the determining the presence of the at least one metal object;
   a light configured to output a light dependent on the determining the presence of the at least one metal object; and
   a vibra configured to vibrate dependent on the determining the presence of the at least one metal object.

16. The apparatus as claimed in claim 13, further comprising a transceiver wherein the controller is configured to control the transceiver dependent on determining the presence of the at least one metal object.

17. The apparatus as claimed in claim 1, further comprising a user interface, wherein the user interface is configured to enable an associated application to start a metal detection feature via the user interface.

18. The apparatus as claimed in claim 17, wherein the metal detection feature is configured to be activated via at least one of a trigger event, a timer, and a sensor output.

19. The apparatus as claimed in claim 17, further comprising an integrated hands free speaker (IHF) including an audio subsystem, wherein the IHF is configured to generate at least one audible tone.

20. The apparatus as claimed in claim 19, wherein the at least one audible tone is dependent on at least one resonance frequency and quality factor (Q factor) associated with the at least one metal object.

21. The apparatus as claimed in claim 17, wherein the user interface output includes at least one of a textual, pictorial, and an icon depiction of a detected metal.

22. The apparatus as claimed in claim 1, wherein the signal processor is further configured to process a change in resonant frequency and quality factor (Q-factor) based on the presence of the at least one metal object as a form of user interface input.

23. The apparatus as claimed in claim 1, wherein the signal processor is further configured to retrieve at least one memorized signal, wherein the at least one memorized signal comprises a quality factor (Q-factor) and resonance frequency associated with a known metal.

24. The apparatus as claimed in claim 1, wherein the signal processor is further configured to cause a change for an acoustic signal based on at least one of a type of metal detected, a change in quality factor (Q-factor), and a change in resonance frequency.

25. The apparatus as claimed in claim 1, wherein the signal processor is further configured to receive a detected magnetic field at the at least one second signal loop, wherein the detected magnetic field is created by the at least one metal object interfering with a generated magnetic field and has a different resonant frequency and quality factor (Q-factor).

26. A method comprising:
   receiving a first signal in at least one first signal loop;
   generating a second signal in at least one second signal loop magnetically coupled with the first signal loop based on induction when the at least one first signal loop receives the first signal and is magnetically coupled with the at least one second signal loop; and
   determining a presence of at least one metal object dependent on induction interference of the at least one metal object on the second signal when the at least one first signal loop is magnetically coupled with the at least one second signal loop.

27. The method as claimed in claim 26, further comprising
   associating at least one memorized resonance profile signal with an identified metal; and
   determining the presence of the at least one metal object dependent on the second signal, where the second signal comprises a resonance profile signal and where determining the presence comprises determining the at least one metal object is the identified metal when the resonance profile signal at least partially matches the at least one memorized resonance profile signal.

28. The method as claimed in claim 26, wherein determining the presence of the at least one metal object dependent on the second signal comprises at least one of:
   determining a composition of metals in the at least one metal object;
   determining a location of the at least one metal object; and
   determining an orientation of the at least one metal object.

29. The method as claimed in claim 26, further comprising providing at least two second signal loops, wherein each of the at least two second signal loops are located or orientated differently to each other; wherein determining the presence of the at least one metal object dependent on the second signal comprises determining a motion of the at least one metal object dependent on the second signal from each of the at least two second signal loops.

* * * * *